(12) United States Patent
Treacy et al.

(10) Patent No.: US 10,137,020 B2
(45) Date of Patent: Nov. 27, 2018

(54) TWO PRONGED HANDLE

(71) Applicant: Cook Medical Technologies LLC, Bloomington, IN (US)

(72) Inventors: Gerard Treacy, County Tipperary (IE); Michael Ryan, Limerick (IE)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 14/949,343

(22) Filed: Nov. 23, 2015

(65) Prior Publication Data

US 2016/0158047 A1 Jun. 9, 2016

Related U.S. Application Data (60) Provisional application No. 62/089,611, filed on Dec. 9, 2014.

(51) Int. Cl.
| | | |
|---|---|---|
| *A61F 2/97* | (2013.01) | |
| *A61F 2/962* | (2013.01) | |
| *A61F 2/954* | (2013.01) | |
| *A61F 2/04* | (2013.01) | |
| *A61M 25/01* | (2006.01) | |
| *A61B 17/34* | (2006.01) | |
| *A61F 2/95* | (2013.01) | |

(52) U.S. Cl.
CPC .......... *A61F 2/962* (2013.01); *A61B 17/3468* (2013.01); *A61F 2/04* (2013.01); *A61F 2/97* (2013.01); *A61M 25/0108* (2013.01); *A61F 2002/044* (2013.01); *A61F 2002/9517* (2013.01)

(58) Field of Classification Search
CPC ......... A61B 17/3468; A61F 2002/9517; A61F 2/962; A61F 2/97; A61F 2002/9528; A61F 2002/9534; A61F 2/954; A61M 2025/0188; A61M 2025/018
See application file for complete search history.

(56) References Cited

U.S. PATENT DOCUMENTS 3,225,762 A * 12/1965 Guttman ........... A61M 25/0606
604/170.02
4,166,469 A * 9/1979 Littleford ............ A61M 25/007
604/164.05

(Continued)

FOREIGN PATENT DOCUMENTS

| EP | 1844739 A1 | 10/2007 |
| WO | WO 2010/120671 A1 | 10/2010 |

OTHER PUBLICATIONS

International Search Report and Written Opinion for related International Application No. PCT/US2015/062079, dated Feb. 17, 2016 (13 pages).

(Continued)

*Primary Examiner* — Seema Mathew
(74) *Attorney, Agent, or Firm* — Brinks Gilson & Lione (57) ABSTRACT

Medical device delivery systems and methods of using the same are disclosed. Some of the delivery systems may include a catheter having a proximal end, a distal end, and a sheath. A bifurcated gripping member may be disposed on the proximal end of the catheter and the bifurcated gripping member may include a first gripping prong and a second gripping prong. A deployable prosthesis may be disposed on the distal end of the catheter.

13 Claims, 4 Drawing Sheets

(56) References Cited

U.S. PATENT DOCUMENTS

| | | | | |
|---|---|---|---|---|
| 4,473,067 A * | 9/1984 | Schiff | | A61M 39/0606 |
| | | | | 600/18 |
| 5,320,602 A | 6/1994 | Karpiel | | |
| 6,190,349 B1 * | 2/2001 | Ash | | A61M 25/0021 |
| | | | | 138/115 |
| 6,517,569 B2 * | 2/2003 | Mikus | | A61M 25/0662 |
| | | | | 623/1.11 |
| 6,780,174 B2 | 8/2004 | Mauch | | |
| 7,048,719 B1 * | 5/2006 | Monetti | | A61M 25/0668 |
| | | | | 604/171 |
| 7,314,481 B2 | 1/2008 | Karpiel | | |
| 9,220,878 B2 * | 12/2015 | Kajii | | A61M 29/00 |
| 2005/0090890 A1 * | 4/2005 | Wu | | A61F 2/95 |
| | | | | 623/1.11 |
| 2007/0016106 A1 * | 1/2007 | Ramaiah | | A61M 25/01 |
| | | | | 600/585 |
| 2007/0078438 A1 * | 4/2007 | Okada | | A61M 25/0032 |
| | | | | 604/523 |
| 2007/0106206 A1 * | 5/2007 | Appling | | A61M 25/0068 |
| | | | | 604/43 |
| 2007/0293937 A1 * | 12/2007 | Biggs | | A61L 27/34 |
| | | | | 623/1.13 |
| 2008/0091137 A1 * | 4/2008 | Reavill | | A61M 25/01 |
| | | | | 604/27 |
| 2009/0157160 A1 * | 6/2009 | Van Der Leest | | A61F 2/95 |
| | | | | 623/1.11 |
| 2009/0270969 A1 * | 10/2009 | Fargahi | | A61F 2/95 |
| | | | | 623/1.11 |
| 2009/0299449 A1 * | 12/2009 | Styrc | | A61F 2/95 |
| | | | | 623/1.11 |
| 2010/0168834 A1 * | 7/2010 | Ryan | | A61F 2/95 |
| | | | | 623/1.11 |
| 2012/0041537 A1 * | 2/2012 | Parker | | A61F 2/95 |
| | | | | 623/1.11 |
| 2012/0059448 A1 * | 3/2012 | Parker | | A61F 2/95 |
| | | | | 623/1.11 |
| 2012/0277576 A1 * | 11/2012 | Lui | | A61M 25/0108 |
| | | | | 600/424 |
| 2014/0121753 A1 | 5/2014 | Jurgen et al. | | |
| 2014/0188211 A1 * | 7/2014 | Roeder | | A61F 2/966 |
| | | | | 623/1.12 |
| 2017/0252190 A1 * | 9/2017 | Becking | | A61F 2/95 |

OTHER PUBLICATIONS

International Preliminary Report on Patentability and Written Opinion for corresponding PCT Application No. PCT/US2015/062079, dated Jun. 13, 2017, 7 pages.

* cited by examiner

TWO PRONGED HANDLE

BACKGROUND

1. Field of the Invention

This disclosure generally relates to medical devices. More particularly, the disclosure relates to a device for delivering and deploying a prosthesis and a method of delivering and deploying the prosthesis.

2. Description of the Related Art

A prosthesis, such as a self-expanding stent, is typically introduced into a patient body using a delivery device that includes an outer sheath coaxially disposed and slidable over an inner catheter. The prosthesis may be disposed at the distal end of the device between the inner catheter and the outer sheath and held in a compressed configuration by the outer sheath. The inner catheter and the outer sheath move coaxially with respect to each other.

If the prosthesis is a self-expanding stent, for example, it may be deployed by pulling back the outer sheath in a proximal direction relative to the inner catheter until the stent is exposed. The self-expanding stent expands from the stent distal end to the stent proximal end as the sheath is proximally withdrawn.

The total length of the medical device may be dictated not only by the length of each component thereof, but also by a length by which the sheath must be withdrawn in order to expose the stent. For example, if the stent is about 100 mm long and completely covered by the sheath, in order to deploy (uncover) the stent, the sheath must be withdrawn in the proximal direction about 100 mm. Thus, the medical device will typically need to be an extra 100 mm long since the sheath will need to be withdrawn by this length to deploy the stent.

Longer medical device lengths pose numerous problems to a physician or operator using the medical device. In general, the longer the medical device, the more difficult to handle and control. Thus, it is advantageous to keep the medical device to a minimal length.

BRIEF SUMMARY

The present disclosure relates to medical delivery systems and methods of using such delivery systems. In one embodiment, the disclosure provides a delivery system comprising a catheter having a proximal end, a distal end, and a sheath slidably disposed on the catheter. A bifurcated gripping member is disposed on the proximal end of the catheter and the gripping member comprises a first gripping prong and a second gripping prong. In some embodiments, a handle is attached to the first gripping prong and the sheath is configured to move (or be withdrawn) along the second gripping prong. In other embodiments, a handle is attached to the second gripping prong and the sheath is configured to move (or be withdrawn) along the first gripping prong.

In another embodiment, the present disclosure provides a method of delivering a prosthesis. The method comprises the step of providing a catheter having a shaft, a proximal end, a distal end, and a sheath slidably disposed on the catheter. The proximal end of the catheter comprises a bifurcated gripping member including a first gripping prong and a second gripping prong. The distal end of the catheter comprises a deployable prosthesis and the sheath surrounds the prosthesis, thereby holding it in a radially compressed configuration. The method also comprises the steps of positioning the distal end of the catheter at a target site in a body and proximally withdrawing the sheath along the catheter shaft and over one of the first gripping prong or the second gripping prong, thereby uncovering and deploying the prosthesis.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

A detailed description of the invention is hereafter described with specific reference being made to the drawings in which.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings or explicitly described below. It should be understood that the drawings are not necessarily to scale, and in certain instances details may have been omitted that are not necessary for an understanding of embodiments disclosed herein, such as conventional fabrication and assembly.

As used in the specification, the terms proximal and distal should be understood as being from the perspective of a physician or operator delivering the prosthesis to a patient. Hence the term "distal" means the portion of the delivery system that is farthest from the physician and the term "proximal" means the portion of the delivery system that is nearest to the physician.

The present disclosure provides a medical device including an improved gripping member. The medical device will be described below in connection with a prosthesis delivery system but it is to be understood that the improved gripping member may be used in connection with any other medical devices incorporating gripping members, such as various endoscopic accessories, including ultrasound needles and snares. The prosthesis to be delivered by the system may be any type of stent, a prosthetic valve device, or any other implantable article.

Figure 1:
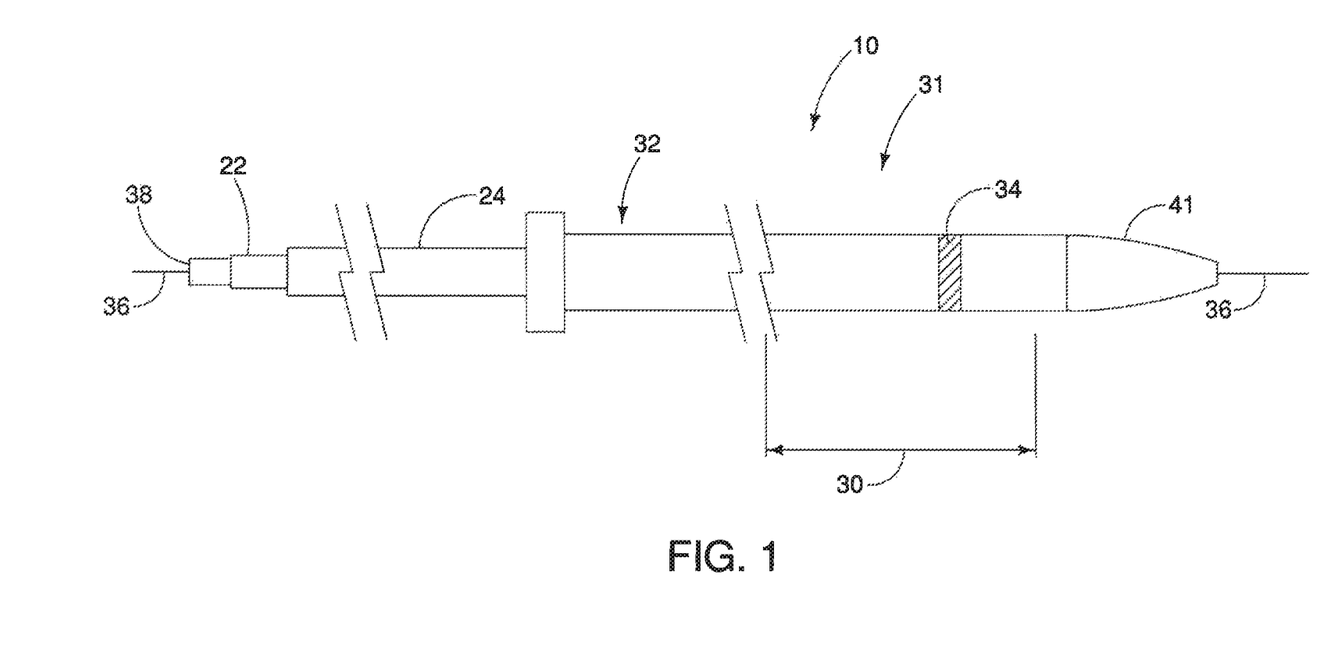
FIG. 1 shows a side view of a distal portion of an embodiment of the presently disclosed delivery system.

One example of a prosthesis delivery system is depicted in FIG. 1. The prosthesis delivery system (10) includes an inner shaft (22) and an outer shaft (24). A gripping portion (not shown), such as the improved gripping member disclosed in the present application, may be located at a proximal end of the system (10). A prosthesis, such as a self-expanding stent, is positionable on a prosthesis nesting region (30) of the inner shaft (22) at a distal portion (31) of the delivery system. The prosthesis delivery system (10) includes a sheath (32) slidably positioned over a portion of the outer shaft (24) and the inner shaft (22) to cover the prosthesis nesting region (30) and a prosthesis disposed thereon. One or more radio-opaque markers (34) may be included on one or more components of the delivery system to indicate the position of the prosthesis in the body. The prosthesis delivery system may also include a stiffening member (36), such as a stylet or wire guide, extendable through a port (38) of the inner shaft (22) through a distal tip (41) at the distal portion (31) of the delivery system (10).

The stiffening member (36), if present, may be removably provided in a lumen of the inner shaft (22). The stiffening member (36) may be provided to help increase the rigidity of the inner shaft (22) against the inward tensioning force of the prosthesis when the prosthesis is in the constrained configuration covered by the sheath (32). In some embodiments, the inner shaft (22) may comprise a soft material to facilitate passage through the body lumen. In the event that the materials are sufficiently soft, the inner shaft (22) may collapse or deform in response to the tensioning force of the prosthesis. In some embodiments, the stiffening member (36) may be a wire guide that can be used to guide the delivery device to the target site.

The stiffening member (36) may comprise any material having suitable stiffness to provide support for the inner shaft (22) with the prosthesis longitudinally tensioned thereon. Exemplary materials for forming the stiffening member (36) may include metal alloys such as stainless steel, tantalum or its alloys, tungsten, platinum, gold, copper, palladium, rhodium, or superelastic alloys, such as nitinol or polymers that can be provided with sufficient shore hardness, such as Pebax®, polyether ether ketone (Peek), polyimide, liquid crystal polymers (LCP) such as Vectran®, polyethylene, polyethylene terephthalate and nylon.

When covered by the sheath (32), the prosthesis is typically in a constrained configuration, collapsed against the inner shaft (22), if an inner shaft is present. If an inner shaft is not present, the prosthesis may be in a constrained configuration within the sheath (32). In some embodiments, the prosthesis is a self-expanding stent and may be configured, for example, as an esophageal stent. An esophageal stent may be from about 60 mm to about 150 mm in length when expanded, for example. However, the prosthesis may be any kind of stent that has a tendency to radially collapse when a longitudinal force is applied to the ends of the stent proximally and distally outward along its central longitudinal axis (centerline).

The sheath (32) may extend distally over the prosthesis abutting a proximal end of the distal tip (41), if present, of the inner shaft (22), if present, forming a smooth outer surface of the delivery system (10). The sheath (32) may be operably connected to a gripping portion, such as the presently disclosed gripping member, of the device. If not connected to a gripping portion, the sheath (32) may include a flange, tab, or other member at or near its proximal end to allow the physician to easily grip the sheath (32) and withdraw in a proximal direction to deploy the prosthesis.

In some embodiments, the presently disclosed gripping member comprises two or more gripping prongs and one or more of the gripping prongs may comprise a handle. If the sheath is connected to the handle, the handle may have a portion that is slidable (or the entire handle may be slidable) such that when the handle or a portion thereof slides in a proximal direction, the sheath also travels toward the proximal end of the delivery system, thereby causing a prosthesis covered by a distal end of the sheath to be exposed, expanded, and deployed.

The sheath may be slit along its long axis to produce a longitudinal channel running from a proximal end of the sheath to its distal end. The entire sheath may include a channel or at least a proximal portion of the sheath may be slit to include a longitudinal channel. In some embodiments, the proximal portion of the sheath covers a length of the sheath extending from the proximal end of the sheath to a midpoint location on the sheath. In some embodiments, the proximal portion comprises from about 10% to about 70% of the entire length of the sheath, such as from about 25% to about 50% of the entire length of the sheath, starting from the proximal end of the sheath.

Instead of a channel, the sheath may include perforations, slits, partial depth grooves, or other modifications making the sheath splittable while being withdrawn. In some embodiments, a blade or sharp projection extending outwardly from the catheter shaft may be provided to cut the sheath as it is withdrawn.

In certain embodiments, the sheath may originally be disposed along a catheter shaft. The sheath may include a tab at its proximal end to enable a physician to readily grasp the sheath and withdraw in a proximal direction. If the gripping member comprises two gripping prongs, e.g. a bifurcated gripping member, the channel, perforations, slits, etc., in the sheath will allow the sheath to approach the bifurcation of the gripping member and slide over one of the gripping prongs.

Figure 2:
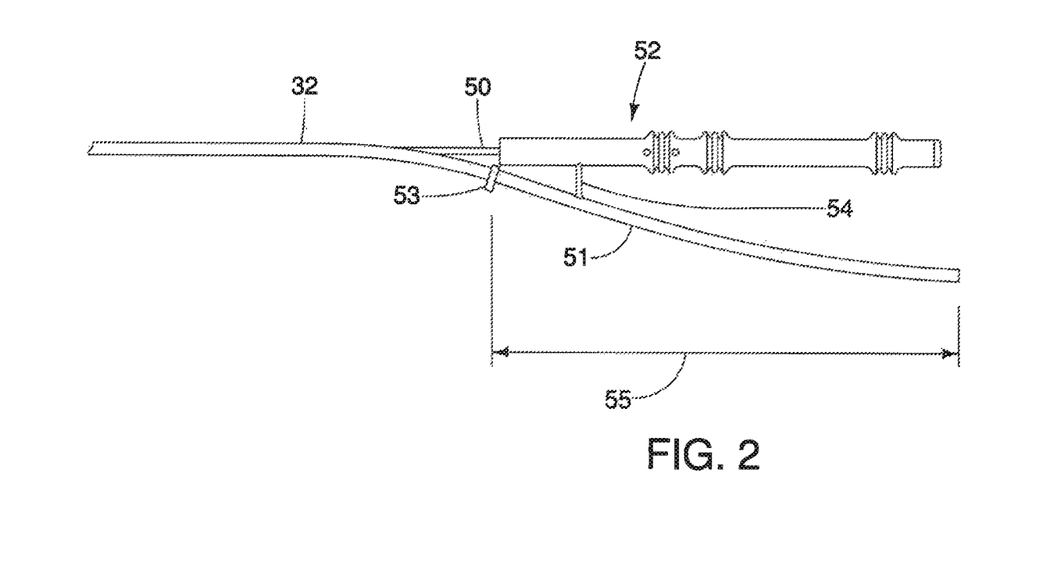
FIG. 2 shows a side view of a proximal portion of an embodiment of the presently disclosed delivery system.

For example, FIG. 2 shows the proximal portion of a prosthesis delivery system including a bifurcated gripping member including a first gripping prong (50) and a second gripping prong (51). The first gripping prong (50) comprises a handle (52). In some embodiments, the delivery system comprises a catheter shaft comprising a distal end and a proximal end, wherein the proximal end splits to form the gripping prongs (50,51) of the bifurcated gripping member.

The sheath (32) as depicted in FIG. 2 comprises a tab (53) at its proximal end. The portion of the sheath (32) comprising the tab (53) is shown disposed on the second gripping prong (51) but the portion of the sheath (32) comprising the tab (53) may also be disposed on the catheter shaft itself, located distally adjacent the bifurcation. In one hand, a physician may grip the handle (52) and in the other hand, the physician may grip the tab (53). The physician may apply longitudinal force to the tab (53), pulling it in a proximal direction, thereby sliding the sheath (32) over the second gripping prong (51). The channel (or perforations) in the sheath (32) allows the sheath to slide over and surround the second gripping prong (51), slide past connecting member (54), which connects the first gripping prong (50) and the second gripping prong (51), and slide all the way to the proximal end of second gripping prong (51), if desired.

Figure 3:
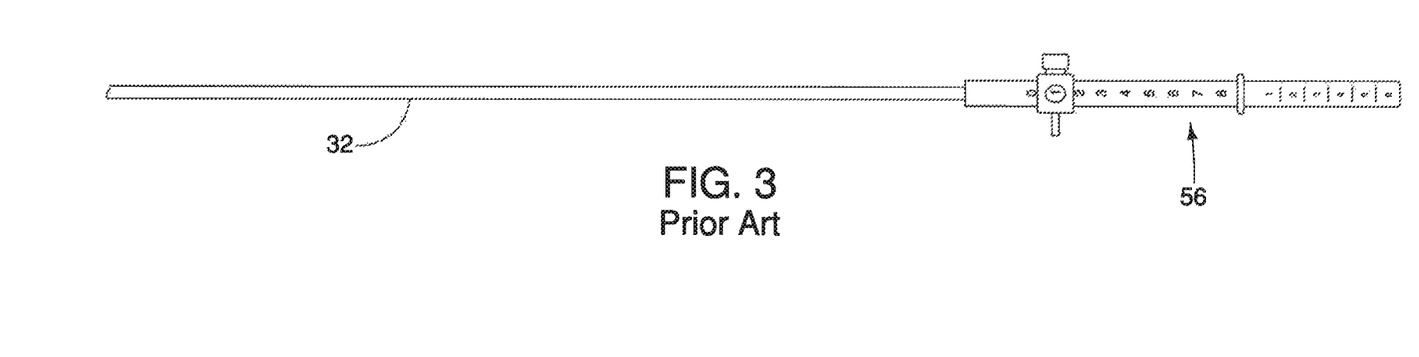
FIG. 3 shows a side view of a proximal portion of a prior art delivery system.

FIG. 3 depicts a delivery system comprising a prior art handle (56). When comparing the grip configurations of FIGS. 2 and 3, it can be seen that the delivery system depicted in FIG. 2 can have a much shorter overall length than the delivery system depicted in FIG. 3. Since it has only a single gripping prong with a handle (56) disposed thereon and the sheath (32) cannot be withdrawn over the handle (56), the system of FIG. 3 must be long enough for the sheath (32) to be withdrawn in a proximal direction so that the distal end (not shown) of the sheath (32) can uncover a prosthesis at the distal end of the delivery system. If the prosthesis to be delivered is, for example, 100 mm long, then the device of FIG. 3 must include at least about 100 mm of extra length so that the sheath (32) may be retracted in a proximal direction to uncover a prosthesis at the distal end of the delivery system. However, with respect to FIG. 2, it can be seen that the travel distance (55) is effectively eliminated by incorporating a bifurcated gripping member and therefore, the overall length of the medical device can be decreased due to the use of the bifurcated gripping member.

Figure 4:
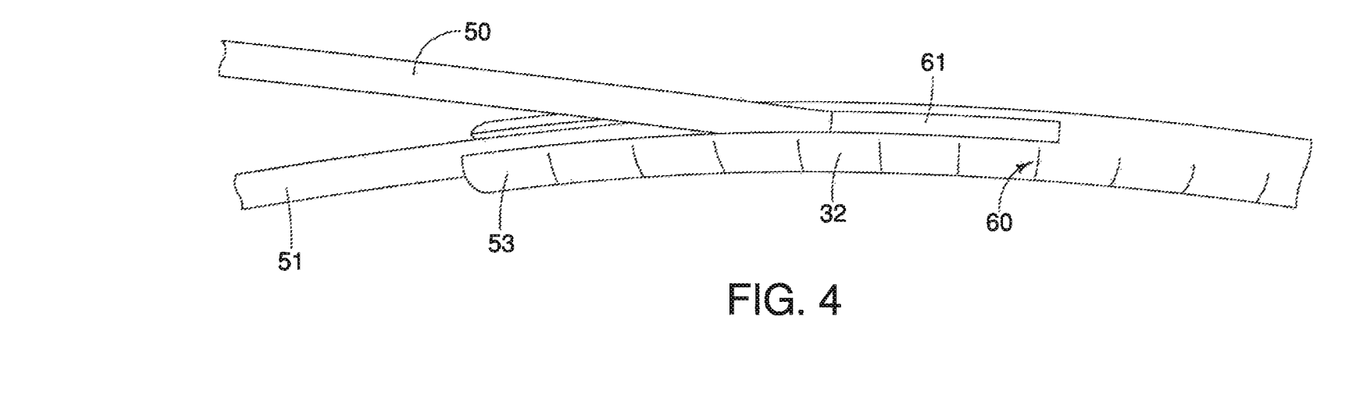
FIGS. 4 and 5 show enlarged views of a portion of a bifurcated gripping member.

As can be seen in FIG. 4, the sheath (32) includes a channel (61) along its longitudinal axis which facilitates movement of the sheath (32) from a location distally adjacent the bifurcation and over the second gripping prong (51). Additionally, the sheath (32) may include one or more slots (60) cut into its body to facilitate bending as it travels over gripping prong (51).

Figure 5:
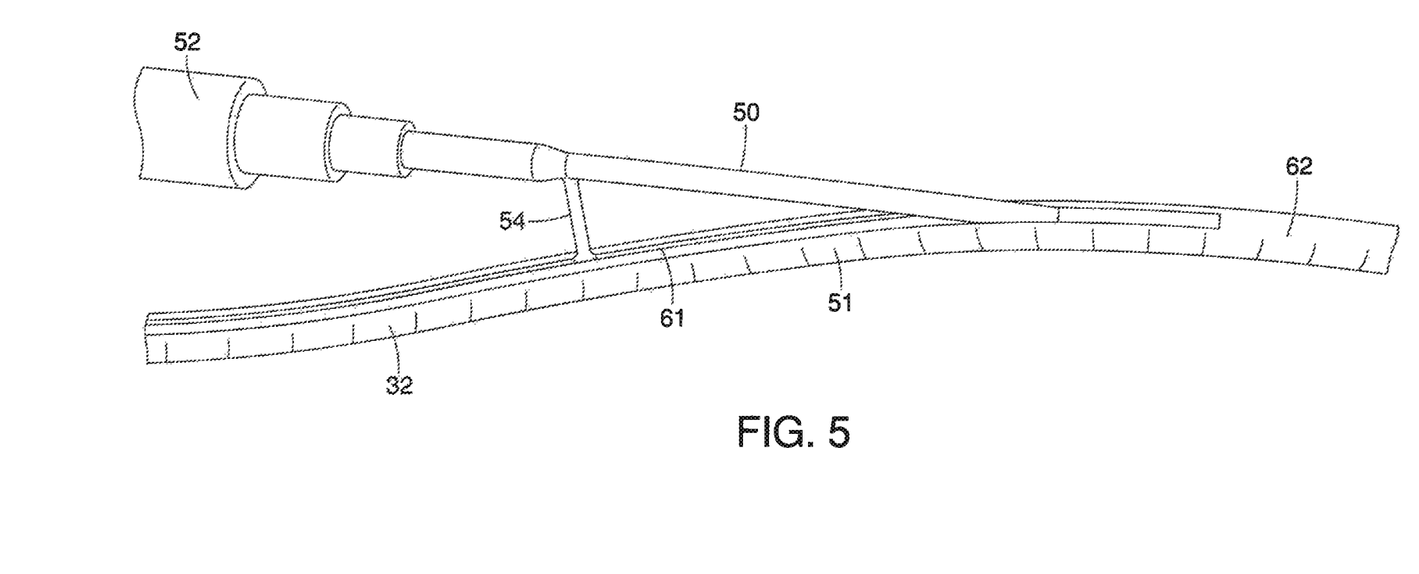

With respect to FIG. 5, the sheath (32) is shown substantially withdrawn in a proximal direction. The proximal end of the sheath (32) may be substantially aligned with and overlap a proximal end of the second gripping prong (51). The sheath (32) depicted in FIG. 5 includes a channel (61) extending longitudinally from its proximal end. As can be seen in the embodiment depicted in FIG. 5, the entire length of the sheath (32) does not comprise a channel (61). That is, a distal portion (62) of the sheath (32) does not comprise a channel. Typically, as noted above, the channel (61) (or perforations) begins at the proximal end of the sheath (32) and extends distally along the length of the sheath (32) to a length that is at least about as long as the prosthesis to be deployed. For example, if the prosthesis to be deployed is a self-expanding stent having a length of about 100 mm, the channel (61) in the sheath (32) should be at least about 100 mm in length, measured from the proximal end of the sheath (32).

Figure 6:
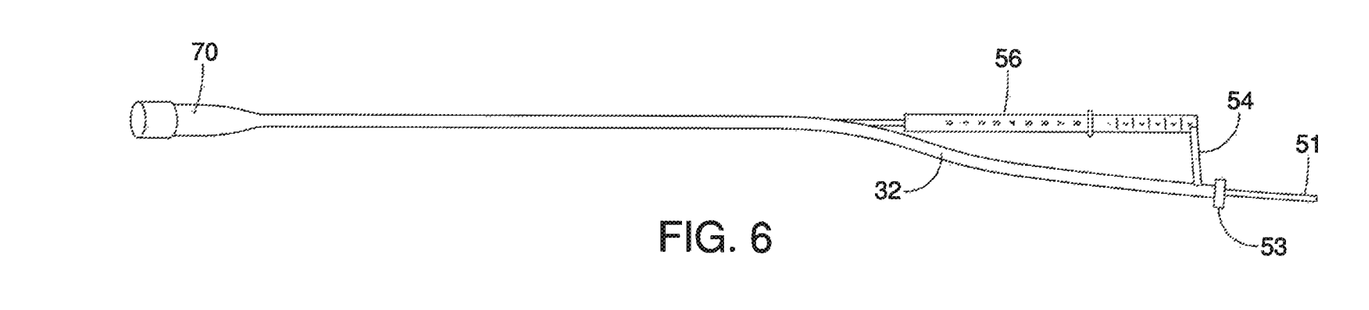
FIGS. 6-8 show side views of prosthesis delivery systems.

FIG. 6 depicts another aspect of a prosthesis delivery system in accordance with the present disclosure. Notably, as compared to the embodiment depicted in FIG. 1, this delivery system does not comprise an outer shaft, distal tip, or a stiffening member. Instead, the delivery system of FIG. 6 comprises a catheter shaft having a proximal end and a distal end. A sheath (32) is disposed on the catheter shaft and the sheath (32) is shown as partially surrounding or covering a self-expanding stent (70). Specifically, a distal end and a mid-section of the self-expanding stent (70) are uncovered by the sheath (32) and have therefore expanded. A proximal end of the self-expanding stent (70) remains covered by the sheath (32), in a radially compressed configuration, and thus cannot be seen.

The proximal end of the self-expanding stent (70) is located distally adjacent a distal end of the catheter shaft. Before beginning the deployment process, the entire self-expanding stent (70) may be covered by the sheath (32). As the sheath (32) is proximally withdrawn, a distal end of the self-expanding stent (70) becomes exposed. Since the proximal end of the self-expanding stent (70) abuts the distal end of the catheter shaft, the self-expanding stent (70) does not move proximally as the sheath (32) is withdrawn as its proximal movement is restricted by the catheter shaft. After continued withdrawal of the sheath (32) in the proximal direction, more of the self-expanding stent (70) becomes exposed and eventually, the sheath (32) may be proximally withdrawn enough to expose the entire self-expanding stent (70) to complete deployment.

The proximal end of the catheter shaft is split to form a bifurcated gripping member having a first gripping prong with a handle (56) disposed thereon and a second gripping prong (51). As with the previous embodiments, as the sheath (32) is proximally withdrawn, its proximal end slides from the catheter shaft over gripping prong (51) and past connecting member (54). The sheath (32) also includes a tab (53) at its proximal end for gripping by a physician or operator of the system.

Figures 7, 8:
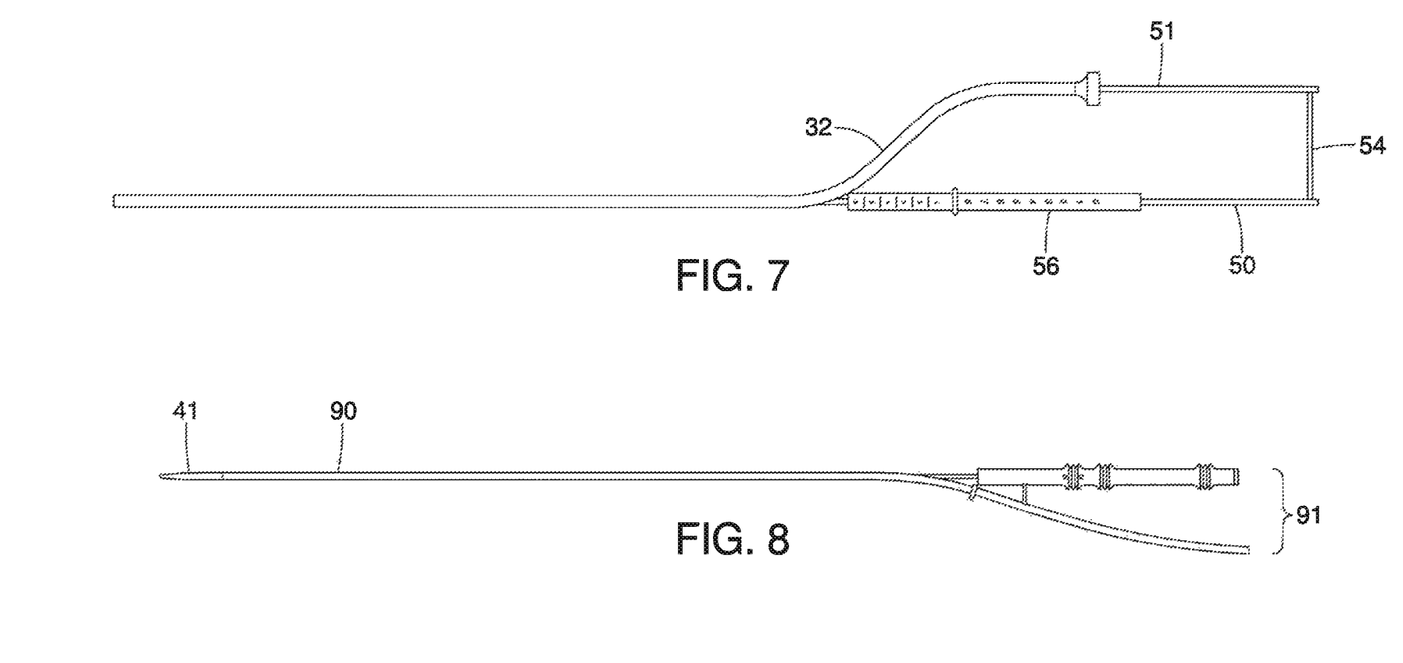

FIG. 7 depicts another aspect of the presently disclosed bifurcated gripping member. As compared to FIG. 6, the first prong (50) is longer than the handle (56) disposed thereon and the connecting member (54) has been moved proximally to connect the proximal ends of the two gripping prongs. The gripping member of FIG. 7 includes a larger distance between the first (50) and second (51) gripping prongs, which may facilitate handling of the delivery system. In either embodiment, the first (50) and second (51) prongs are substantially parallel.

An additional embodiment is depicted in FIG. 8. The delivery system of FIG. 8 includes a catheter shaft (90) having a distal tip (41) at its distal end and a bifurcated gripping member (91) at its proximal end. A prosthesis may be disposed at the distal end of the catheter shaft (90). Specifically, a distal end of the prosthesis may be located proximally adjacent a proximal end of the distal tip (41). A sheath may be disposed on the catheter shaft (90) and cover the prosthesis located proximally adjacent the distal tip (41). As in other embodiments, as the sheath is proximally withdrawn, the prosthesis becomes exposed and may be delivered to the target site in the body.

The materials used to manufacture the components of the medical devices disclosed herein may be any materials known to one skilled in the art that are suitable for use in patients. By way of non-limiting example, the shafts, distal tips, handles, connecting members, gripping prongs, and sheaths may be formed from polytetrafluoroethylene (PTFE) or stainless steel. Nylon and high-density polyethylene (HDPE) may also be used. Additional materials include, polyethylene ether ketone (PEEK), fluorinated ethylene propylene (FEP), perfluoroalkoxy polymer resin (PFA), polyamide, polyurethane, low density polyethylene, including multi-layer or single layer structures and may also include reinforcement wires, braid wires, coils, coil springs and or filaments.

In one embodiment, the first and second prongs of the gripping member may be formed from a stainless steel cannula and the prongs may merge into a single cannula/catheter shaft.

Some of the components, such as the stents and stiffening members, may be formed from nickel titanium alloys, such as nitinol, stainless steel, cobalt alloys and titanium alloys. In some embodiments, the components, such as the stents, may comprise biodegradable materials. A number of bioabsorbable homopolymers, copolymers, terpolymers, or blends of bioabsorbable polymers are known in the medical arts. These include, but are not limited to, polyesters including poly-alpha hydroxy and poly-beta hydroxy polyesters, polycaprolactone, polyglycolic acid, polyether-esters, poly (p-dioxanone), and polyoxaesters; polyphosphazenes; polyanhydrides; polycarbonates including polytrimethylene carbonate and poly(iminocarbonate); polyesteramides; polyurethanes; polyisocyanates; polyphosphazines; polyethers including polyglycols; polyorthoesters; epoxy polymers including polyethylene oxide; polysaccharides including cellulose, chitin, dextran, starch, hydroxyethyl starch, polygluconate, hyaluronic acid; polyamides;

polyamino acids; polyester-amides; polyglutamic acid; poly-lysine; gelatin; fibrin; fibrinogen; casein; collagen; and any combination thereof.

In some embodiments, the stents may comprise a woven mesh formed from a metal, a polymer, or a laser cut pattern formed in a metal stent. One example of a woven stent is the EVOLUTION® stent (Wilson-Cook Medical, Inc.). Other suitable biocompatible materials may also be used for any of the components described herein.

An exemplary method using the presently disclosed bifurcated gripping member in connection with a self-expanding stent delivery device will now be described. However, it should be noted that the bifurcated gripping member may be used in connection with any medical device where it could prove to be advantageous and the methods disclosed herein are not limited to using the bifurcated gripping member in connection with a stent delivery system.

The stent delivery system may be provided in a sterile packaging. The stent may be provided separately in an expanded configuration or it may be provided within a sheath, in a constrained configuration. Some stent materials may weaken or otherwise deform when stored in a constrained configuration so providing the stent separately, in an expanded configuration may be advantageous. If the stent is provided separately in its expanded configuration, it may subsequently be disposed around a stent nesting region of the catheter shaft and the sheath may be manually placed over the stent to hold the stent in its constrained configuration. Alternatively, the catheter shaft may not comprise a stent nesting region so the proximal end of the stent may be aligned with the distal end of the catheter shaft and the sheath may be placed over the stent to hold it in a constrained configuration.

In some embodiments, the sheath may include different sets of distance measurement markings, such as two different sets, one to be used when the sheath is covering the stent and one set to be used when the sheath has been proximally withdrawn to uncover the stent. The markings may be of different colors, for example, to easily identify the two measurements. The stent delivery system may be inserted into a patient's alimentary canal via the mouth using the first set of sheath markings to place the constrained stent in the stricture by measuring the distance relative to the incisor teeth. Once at the target location within the body, the sheath may be proximally withdrawn to expose and deliver the stent.

As noted above, the delivery system may comprise a bifurcated gripping member having a first gripping prong and a second gripping prong. Before delivery of the stent, the proximal end of the sheath may be located on the catheter shaft distally adjacent the bifurcation. Alternatively, before delivering the stent, the proximal end of the sheath may be located on one of the gripping prongs. In any event, before delivery, the sheath surrounds and covers the stent and a substantial portion, if not all, of the catheter shaft. Once the stent arrives at the target location within the body, the sheath is proximally withdrawn over one of the gripping prongs, thereby exposing the stent and allowing it to expand at the target site.

In some embodiments, an endoscope may be positioned within the patient's lumen so the operator can view the proximal side of the stricture. A guidewire may then be inserted through the stricture and the endoscope may be removed. The proper length stent is selected based on the stricture measurement. The operator inserts the distal portion of the stent delivery system into the patient's lumen with the stent in the constrained configuration within the sheath. The guidewire may be inserted first to navigate a tortuous pathway to the treatment site and the system is delivered over the guidewire to the treatment site. In some embodiments, an endoscope may then be placed into the patient's lumen adjacent and parallel to the system. Alternatively, the stent delivery system may be inserted into the patient's lumen through the working channel of an endoscope, depending on the size and location of the lumen.

A viewing port of the endoscope may be used to identify the proximal end of the stricture at the treatment site. The stent is positioned within the lumen at the treatment site. For embodiments comprising a soft inner shaft, a stiffening member may be inserted through the lumen of the inner shaft to provide support for the longitudinally tensioned stent. Once the proper position for the stent is achieved within the patient's lumen, the sheath is proximally withdrawn and the stent expands and is exposed within the patient's lumen. The delivery system, and endoscope, if present, may then be removed from the patient's body.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a device" is intended to include "at least one device" or "one or more devices."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A delivery system comprising:
    a catheter having a proximal end and a distal end and an outermost surface extending there between, wherein the distal end comprises a deployable prosthesis;
    a sheath slidably disposed about the outermost surface of the catheter; and
  a bifurcated gripping member disposed on the proximal end of the catheter,
    wherein the gripping member comprises a first stationary gripping prong and a second stationary prong, the first stationary gripping prong and the second stationary prong connected by a connection member, and wherein the first gripping prong comprises a handle configured to be grasped by a user and wherein a proximal end of the sheath is retracted proximally over, and generally conforms to, the shape of an outermost surface of the second stationary prong.

2. The delivery system of claim 1, wherein the deployable prosthesis is a self-expanding stent.

3. The delivery system of claim 2, wherein the self-expanding stent is surrounded by the sheath and held in a constrained configuration by the sheath.

4. The delivery system of claim 3, wherein a proximal end of the self-expanding stent is located distally adjacent the distal end of the catheter.

5. The delivery system of claim 3, wherein the self-expanding stent is disposed on a prosthesis nesting region near the distal end of the catheter.

6. The delivery system of claim 2, wherein the self-expanding stent is an esophageal stent having an expanded length of about 60 mm to about 150 mm.

7. The delivery system of claim 1, wherein the sheath comprises a longitudinal channel.

8. The delivery system of claim 1, wherein a distal end of the sheath comprises a radio-opaque marker or wherein the distal end of the catheter comprises a distal tip.

9. The delivery system of claim 1, wherein the catheter comprises a longitudinal lumen extending therethrough, further wherein the longitudinal lumen comprises a stiffening member.

10. The delivery system of claim 1, wherein at least one of the catheter and the bifurcated gripping member comprises stainless steel.

11. The delivery system of claim 1, wherein the proximal end of the sheath comprises a tab.

12. The delivery system of claim 1, wherein the sheath comprises perforations, slits, or partial depth grooves.

13. The delivery system of claim 1, wherein the proximal end of the catheter comprises a blade or sharp projection extending outwardly therefrom.

* * * * *